United States Patent
Chopdekar et al.

(10) Patent No.: US 7,754,875 B1
(45) Date of Patent: *Jul. 13, 2010

(54) HALIDE-FREE GLUCOSAMINE BASE-ORGANIC ACID SALT COMPOSITIONS

(75) Inventors: Vilas M Chopdekar, Edison, NJ (US); Mary P. Camaga, Wayne, NJ (US)

(73) Assignee: JFC Technologies, LLC, Bound Brook, NJ (US)

( * ) Notice: Subject to any disclaimer, the term of this patent is extended or adjusted under 35 U.S.C. 154(b) by 1246 days.

This patent is subject to a terminal disclaimer.

(21) Appl. No.: 11/223,666

(22) Filed: Sep. 9, 2005

Related U.S. Application Data

(60) Provisional application No. 60/611,189, filed on Sep. 17, 2004.

(51) Int. Cl.
*C07H 5/04* (2006.01)
*C07H 5/06* (2006.01)
(52) U.S. Cl. .................. 536/55.2; 536/55.3; 514/62
(58) Field of Classification Search ............... 536/55.2, 536/55.3; 514/62
See application file for complete search history.

(56) References Cited

U.S. PATENT DOCUMENTS

| | | | | |
|---|---|---|---|---|
| 5,877,212 | A * | 3/1999 | Yu et al. | 514/557 |
| 5,902,801 | A * | 5/1999 | Schleck et al. | 514/62 |
| 6,159,485 | A | 12/2000 | Yu et al. | 424/401 |
| 6,191,167 | B1 | 2/2001 | Yu et al. | 614/558 |
| 6,384,079 | B1 | 5/2002 | Yu et al. | 514/577 |
| 6,514,507 | B2 | 2/2003 | Malgnan et al. | 424/401 |
| 6,524,593 | B1 | 2/2003 | Yu et al. | 424/401 |
| 6,630,442 | B1 * | 10/2003 | Hersh | 514/2 |
| 7,141,556 | B2 * | 11/2006 | Vila Pahi et al. | 514/62 |
| 7,388,000 | B1 * | 6/2008 | Redkar et al. | 514/62 |
| 7,388,001 | B1 * | 6/2008 | Chopdekar et al. | 514/62 |
| 2004/0092482 | A1 | 5/2004 | Gupta | 514/62 |

FOREIGN PATENT DOCUMENTS

GB    A 1198274    7/1970

* cited by examiner

*Primary Examiner*—Shaojia Anna Jiang
*Assistant Examiner*—Everett White
(74) *Attorney, Agent, or Firm*—Jack Matalon

(57) ABSTRACT

A salt of a glucosamine base having a purity of at least about 99 wt. % and a maximum halide content of about 0.01 wt. %, and an organic acid. The organic acid that is saltified with the glucosamine base is preferably a hydroxyacid or a ketoacid. Preferably, the salt is stabilized by coating the salt with at least one pharmaceutically acceptable polymer comprising a water-soluble, water-immiscible and/or water-swellable homopolymer and/or copolymer. Suitable polymers include carboxypolymethylene homopolymers and copolymers; polyethylene glycol homopolymers and copolymers; polypropylene glycol homopolymers and copolymers; ethylcellulose; povidone homopolymers and copolymers; polyacrylic acid homopolymers and copolymers; polyacrylamide homopolymers and copolymers; polysaccharides; and mixtures of two or more of the foregoing polymers. The resultant coated salt composition will be stable at ambient temperatures and upon exposure to the atmosphere.

19 Claims, No Drawings

HALIDE-FREE GLUCOSAMINE BASE-ORGANIC ACID SALT COMPOSITIONS

CROSS-REFERENCE TO RELATED APPLICATION

This application claims the benefit of provisional application Ser. No. 60/611,189 filed Sep. 17, 2004.

FIELD OF THE INVENTION

The invention relates to salts of a halide-free glucosamine base and an organic acid and to methods for preparing such salts. The organic acids preferably are hydroxyacids or ketoacids. The salt compositions are useful for incorporation in pharmaceutically acceptable topically applied dermatologic and cosmetic formulations.

BACKGROUND OF THE INVENTION

Glucosamine is a well-known amino monosaccharide found in chitin, glycoproteins and glycosaminoglycans. Unfortunately, pure glucosamine derivatives containing neither any halides (e.g., chloride, iodide, etc.) nor any cations (e.g., calcium, potassium, sodium, etc.) are not currently available. What is currently available in the marketplace is a glucosamine halide salt such as glucosamine hydrochloride or glucosamine hydroiodide or mixtures of salts together with glucosamine. Mixed salts of glucosamine hydrochloride and alkaline or earth alkaline metal sulfates or phosphates are well known. Such mixed salts are used rather than glucosamine phosphate alone since the latter is unstable in view of its highly hygroscopic nature and the facility with which its amino group oxidizes if not completely saltified, see, e.g., U.S. Pat. No. 4,642,340 and U.S. Pat. No. 3,683,076 which disclose mixtures of glucosamine phosphate and glucosamine hydroiodide.

In EP 0 214 642, free glucosamine base containing residual chloride is converted to a mixed salt of glucosamine phosphate and potassium chloride by dissolving the glucosamine base in water, adding a stoichiometric quantity of concentrated sulfuric acid to form a solution of glucosamine phosphate in water and dissolving a stoichiometric amount of potassium chloride in the solution. The mixed salt is precipitated from the solution by addition of a precipitant such as isopropanol, stirring the mixture for about 14 hours to complete the precipitation, cooling the reaction mass to 0° C. and recovering the precipitated salt by filtration. This process results in low yields.

Topically applied cosmetic and dermatologic formulations containing hydroxy-acids are well known in the prior art, e.g., see U.S. Pat. Nos. 2,118,566; 3,124,506; 3,666,863; 3,879,537; and the like U.S. Patent Application 2004/0092482 A1 and U.S. Pat. No. 5,877,212 disclose the preparation of complexes of glucosamine and hydroxyacids and their use in topically applied cosmetic and dermatologic formulations. However, such compositions are disadvantageous since they contain a halide such as sodium or potassium chloride. This results from the fact that glucosamine is only available as the hydrochloride salt regardless of whether it is extracted from shellfish or manufactured by a fermentation process. When the glucosamine hydrochloride is neutralized with a base such as sodium or potassium hydroxide to release the glucosamine free base, the composition will necessarily also contain sodium or potassium chloride. Since both the free glucosamine base and the halide salt are both fully soluble in water, it has not been possible to prepare halide-free glucosamine base.

In co-pending patent application Ser. No. 11/223,336, filed Sep. 9, 2005 (corresponding to provisional patent application Ser. No. 60/611,709, filed Sep. 17, 2004), the disclosure of which is incorporated herein in its entirety by reference, a process is disclosed for converting a glucosamine halide salt into a halide-free glucosamine base. The resultant halide-free glucosamine base may then be used as is for those medicinal purposes in which the presence of a salt such as sodium or potassium chloride, sodium or potassium phosphate, sodium or potassium iodide, etc. is undesirable. The halide-free glucosamine base may also be employed to prepare a wide variety of useful derivatives such as glucosamine salts, e.g., glucosamine phosphate, glucosamine sulfate, n-acetylglucosamine, glucosamine salts of drugs having acidic functionalities, the glucosamine base-organic acid salts of the invention, etc., wherein such derivatives do not contain any objectionable halide or cations such as sodium or potassium.

The halide-free glucosamine base prepared by the process disclosed in the above-identified co-pending provisional application may be readily converted into a salt of the glucosamine base and an organic acid by the process described below. However, the resultant salt may be unstable—it may decompose when exposed to ambient temperatures and/or the atmosphere. Therefore, some of the glucosamine base-organic acid salts must be kept refrigerated in a closed container, thereby limiting the usefulness of the compositions.

It would be most desirable if a method could be found for stabilizing the halide-free glucosamine base-organic acid salts without having any adverse effect on the physical and chemical properties of the salts such that the salts could be exposed to the atmosphere and stored at ambient temperatures without decomposition occurring.

DETAILS OF THE INVENTION

The invention relates to halide-free glucosamine base-organic acid salts, stabilized halide-free glucosamine base-organic acid salt compositions and to methods for preparing such salts and such compositions. The preferred organic acids for use in preparing the salts of the invention are the hydroxyacids and the ketoacids containing 2 to 30 carbon atoms. Not only are the glucosamine-organic acid salts of the invention free of halide, but also they are also free of the salts that are present in currently available "glucosamine" compositions such as those described in U.S. Pat. Nos. 5,843,923, 5,902,801 and 6,472,380. Thus a person who cannot or who does not wish to use a skin formulation containing alkali and/or alkaline earth metal salts in current formulations containing "glucosamine" may now be able to use formulations prepared from halide-free glucosamine base-organic acid salts that contain neither extraneous cations such as sodium, potassium, etc. nor extraneous anions such as halides, sulfates, etc.

The starting material for preparing the glucosamine base-organic acid salts of the invention comprises a halide-free glucosamine base that may be prepared by the method disclosed in the above-identified co-pending patent application. Such method involves the following steps:

(a) a glucosamine halide salt (e.g., glucosamine hydrochloride, glucosamine hydroiodide, etc.) is reacted with a lithium base in the presence of a $C_1$-$C_4$ alcohol to thereby generate a $C_1$-$C_4$ alcohol solution of a lithium halide and an insoluble halide-free glucosamine base; and (b) the insoluble halide-free glucosamine base is separated from the $C_1$-$C_4$ alcohol solution of the lithium halide salt.

For maximum yields, the reaction should be carried out at a temperature of about 15 to about 35° C.; conveniently, the reaction may be carried out at ambient temperatures.

The $C_1$-$C_4$ alcohol may be methanol, ethanol (preferably anhydrous) or isopropanol; the preferred alcohol comprises methanol. The lithium base may be anhydrous lithium hydroxide, lithium hydroxide monohydrate, lithium methoxide, lithium ethoxide or lithium isopropoxide. The preferred lithium base comprises anhydrous lithium hydroxide. It has been found that the presence of water in the reaction mixture reduces the yield of the halide-free glucosamine base. Accordingly, it is preferred that the reaction be carried out under anhydrous conditions. In general, the lithium base is employed in an amount of about 1.0 to about 1.2 moles per mole of halide present in the glucosamine halide salt. Excess lithium base is unnecessarily wasteful and will reduce the yield of the halide-free glucosamine base. Typically, the alcohol is employed in an amount of about 1 to about 10 parts, preferably 3 to 6 parts, per part of lithium base.

After allowing the reaction to proceed (preferably with agitation) for about 5 minutes to about 2 hours, the solid halide-free glucosamine base is filtered off from the resultant alcohol solution of the lithium halide and washed with additional alcohol. The halide-free glucosamine base may then be dried under vacuum at a temperature of about 15 to about 30° C. The yield typically ranges from about 85 to about 90%. The halide-free glucosamine base is quite pure. It will have a purity level of greater than about 99 wt. % and the maximum halide content will be 0.01 wt. %, e.g., 100 ppm or less and very often, the halide content will be less than 50 ppm. Based upon the residual halide content of the halide-free glucosamine base, the lithium residue in the glucosamine base will generally be 20 ppm or less and often, the lithium residue content will be less than 10 ppm.

The halide-free glucosamine base is quite hygroscopic and will decompose over a period of time if exposed to ambient temperature and/or to the atmosphere. Accordingly, it should be refrigerated in a closed container or preferably promptly used after recovery for conversion to the halide-free glucosamine base-organic acid salt compositions of the invention as described below.

The halide-free glucosamine base may be readily converted to the salts of the invention by reacting the halide-free glucosamine base in water with a stoichiometric amount of the desired organic acid. Typically, the reaction mixture will comprise the glucosamine base, the desired organic acid and about 5 to about 30 parts, preferably 15 to 20 parts, of water) preferably purified water) per total parts of the glucosamine base and organic acid. Although lesser amounts of water may be employed, the resultant solutions may become too viscous to be properly agitated, particularly if the halide-free glucosamine base-organic acid salt composition is not isolated from the reaction mixture, but is stabilized by the addition of a polymer to the reaction mixture, as described below. On the other, hand, excessive amounts of water may lead to reduced yields if a water-miscible solvent is used to recover the composition and if freeze-drying is used to recover the composition, the freeze-drying process becomes more time-consuming and expensive because of the large amount of water to be removed from the reaction mixture.

The desired organic acid is generally present in a stoichiometric amount based on the number of moles of glucosamine base present in the reaction mixture (one mole of the organic acid will be required per mole of the base; if the desired organic acid contains more than one acid functionality, the molar ratio of the glucosamine base to the selected organic acid should be adjusted accordingly. The desired organic acid is slowly added to the aqueous solution of the glucosamine base while the aqueous solution is agitated, e.g. over a period of a few minutes, and the reaction mixture is further agitated for 5 to 120 minutes. The reaction is typically conducted at a temperature of about 15 to about 40° C. (the reaction is slightly exothermic). Thereafter, the glucosamine base-organic acid salt of the invention may be recovered from the reaction mixture by freeze-drying or by adding a water-miscible solvent such as acetone to the reaction mixture such that the salt will precipitate from the reaction mixture and the salt is then recovered by conventional filtration methods. The salt may then be dried by conventional methods, e.g., a stream of nitrogen, a vacuum oven at 30-50° C. for a period of 1 to 10 hours, etc. It is preferred that the recovery of the salts of the invention be carried out by a freeze-drying process as described in greater detail below.

Some of the glucosamine base-organic acid salts of the invention may be decompose over a period of time if they are exposed to ambient temperatures or the atmosphere. Therefore, it is preferred that the glucosamine base-organic acid salt not be recovered from the reaction mixture as is, but converted to a stabilized form prior to recovery. Conversion of the salt to its stabilized form may be desirable even for those salts that do not decompose upon exposure to ambient temperatures or the atmosphere, since the pharmaceutically acceptable polymers employed in stabilizing, i.e., coating, the salts of the invention may provide extended-release properties when dermatological and/or cosmetic formulations containing the salts are topically applied.

Stabilization of the glucosamine base-organic acid salt is readily accomplished by adding a suitable pharmaceutically acceptable polymer to the reaction mixture prior to recovery of the salt. The pharmaceutically acceptable polymer may be a water-soluble, water-dispersible and/or or a water-swellable homopolymer and/or copolymer. Preferably,. the pharmaceutically acceptable polymer will be water-soluble. In general, the polymer will be employed in an amount of about 2 to about 70, preferably 20 to 50, parts by weight of the polymer per part of the salt. Nonlimiting examples of commercially available pharmaceutically acceptable homopolymers and copolymers suitable for stabilizing the salt include the following: carboxypolymethylene homopolymers and copolymers, i.e., vinyl polymers having active carboxyl groups such as high molecular weight homopolymers of acrylic acid crosslinked with allylsucrose or allylpentaerythritol and copolymers of acrylic acid modified by long chain ($C_{10}$-$C_{30}$) alkyl acrylates and crosslinked with allylpentaerythritol— such polymers are commercially available and are marketed as Carbopol® polymers; polyethylene glycol homopolymers and copolymer (e.g., polyethylene-co-lactic acid copolymers), particularly polyethylene glycol polymers having molecular weights in the range of about 2,000 to about 20,000, preferably 4,000 to 18,000; polypropylene glycol homopolymers and copolymers, especially polypropylene glycol homopolymers having molecular weights of about 800 to about 18,000; ethylcellulose; povidone homopolymers, i.e., synthetic water-soluble homopolymers of N-vinyl-pyrrolidone, especially those having a molecular weight of about 2,500 to about 10,000; copovidone, i.e. synthetic random copolymers of N-vinylpyrrolidone and vinyl acetate in a 60:40 ratio; polyacrylic acid homopolymers and copolymers; polyacrylamide homopolymers and copolymers; polysaccharides; etc.

The choice of particular homopolymers and/or copolymers for coating, i.e., stabilizing, the glucosamine base-organic acid salt, is not critical so long as the polymers are pharmaceutically acceptable, have the capability of coating, i.e., stabilizing, the salt without any adverse chemical reaction occurring between the selected polymer and the salt, and the resultant coated composition is stable, i.e., it will not undergo decomposition when exposed to ambient temperatures or the atmosphere.

If the glucosamine base-organic acid salt is to be recovered from the reaction mixture in a stabilized form, the desired pharmaceutically acceptable polymer is added, preferably in increments, with stirring, to the aqueous glucosamine base solution. This step will generally take about 5 to about 15 minutes and is preferably conducted at a temperature of about 15 to about 40° C. After all increments of the selected polymer have been added, stirring is continued for an additional 5 to 120 minutes. Thereafter, the organic acid is slowly added to the reaction mixture, while maintaining the reaction mixture at a temperature of about 15 to 40° C.

The last step is the recovery of the polymer-coated, i.e., stabilized, glucosamine base-organic acid salt composition from the reaction mixture. The stabilized glucosamine base-organic acid salt composition is recovered from the reaction mixture by freeze-drying or by adding a water-miscible solvent, e.g., acetone, to the reaction mixture to cause the stabilized composition to precipitate out from the reaction mixture. The precipitate is then recovered by conventional filtration methods and it may be dried as described below. Of course, the choice of stabilizing polymer and water-miscible solvent should be such that the polymer will not dissolve in, or otherwise react with, the solvent.

The stabilized glucosamine base-organic acid salt composition is preferably recovered by removal of water from the reaction mixture by freeze-drying, a well-known technique for removing water from compositions. Although freeze-drying is a time-consuming process, (a reaction mixture containing one liter of water will typically require 30-36 hours to remove about 97% of the water), it is preferred since the formation of decomposition products resulting from heating the reaction mixture or adding solvents to the reaction mixture can be avoided.

The freeze-drying process will generally be carried out at a reduced pressure and reduced temperature, e.g., a pressure of not greater than 500 milliTorre, preferably 300 to 100 milliTorre and at a temperature of about −60 to about −20° C., preferably −50 to −40° C. The endpoint of completion of the freeze-drying process may be determined by condensing and measuring the quantity of water removed during the freeze-drying process. The time required for completion of the freeze-drying process will vary depending on factors such as pressure, temperature, quantity of reaction mixture to be free-dried, level of water to be tolerated in the stabilized halide-free glucosamine base-organic acid salt composition, the thickness and surface area of the reaction mixture in the trays of the freeze-drying equipment, etc.

If the stabilized glucosamine base-organic acid salt composition is to be recovered by precipitation from the reaction mixture by addition of a water-miscible solvent such as acetone to the reaction mixture, generally about 2 to about 10 parts of solvent per part of reaction mixture will be required.

After the stabilized glucosamine base-organic acid salt composition has been recovered from the reaction mixture, it may be dried by conventional techniques, e.g., a stream of nitrogen, vacuum oven at a temperature of about 30 to about 50° C. for 1 to 10 hours or more, etc.

A wide variety of suitable organic acids may be used to form the salts of the invention. Preferably, the organic acid is a hydroxyacid or a ketoacid. The following is a nonlimiting, representative list of suitable hydroxyacids and ketoacids:

Alkyl Alpha Hydroxyacids glycolic acid; lactic acid; methyllactic acid; 2-hydroxybutanoic acid; 2-hydroxypentanoic acid; 2-hydroxyhexanoic acid; 2-hydroxyheptanoic acid; 2-hydoxyoctanoic acid; 2-hydroxynonanoic acid; 2-hydroxydecanoic acid; 2-hydroxyundecanoic acid; 2-hydroxydodecanoic acid; 2-tetradecanoic acid; 2-hexadecanoic acid; 2-hydroxyoctadecanoic acid; 2-hydroxy-eicosanoic acid; 2-hydroxytetraeicosanoic acid; 2-hydroxytetraeicosenoic acid; 2,4-di-hydroxy-3,3-dimethylbutanoic acid; glyceruronic acid; erythruronic acid; threuronic acid; 2,3,4-trihydroxypentanuronic acid; 2,3,4,5-tetrahydroxyhexanuronic acid; 2,3,4,5,6-pentahydroxyheptanuronic acid; quinic acid; piscidic acid; lactobionic acid; ascorbic acid; isoascorbic acid; 2-hexulsonic acid; and 5-hexulsonic acid.

Aralkyl and Aryl Alpha Hydroxyacids mandelic acid; benzilic acid; phenylacetic acid; atrolactic acid; and 4-hydroxymandelic acid.

Polyhydroxy Alpha Hydroxyacids glyceric acid; 2,3,4-trihydroxybutanoic acid; 2,3,4,5-tetrahydroxypentanoic acid; 2,3,4,5,6-pentahydroxyhexanoic acid; and 2,3,4,5,6,7-hexahydroxyheptanoic acid.

Polycarboxylic Alpha Hydroxyacids tartronic acid; malic acid; citramalic acid; tartaric acid; 2,3,4-trihydroxypentane-1,5-dioic acid; 2,3,4,5-tetrahydroxyhexane-1,6-dioic acid; citric acid; isocitric acid; homoisocitric acid; and n-hexadecylcitric acid.

Beta Hydroxyacids 3-hydroxypropanoic acid; 3-hydroxybutanoic acid; tropic acid; trethocanic acid; and aleuritic acid.

Ketoacids glyoxylic acid; pyruvic acid; benzoylformic acid; phenylpyruvic acid; 2-ketobutanoic acid; 2-ketopentanoic acid; 2-ketohexanoic acid; 2-ketoheptanoic acid; 2-ketooctanoic acid; and 2-ketododecanoic acid.

The glucosamine base-organic acid salts of the invention are particularly useful when formulated alone, or with other therapeutic agents, into pharmaceutically acceptable carriers, e.g., lotions, creams, ointments, salves, shampoos, etc. The resultant products are especially useful for topical dermatological and cosmetic applications.

The following nonlimiting examples shall serve to illustrate the preferred embodiments of the invention. Unless otherwise indicated, all parts and percentages are on a weight basis.

EXAMPLE 1

17.9 g of halide-free glucosamine base was mixed with 150 cc of purified water in a reaction vessel. After a clear solution was obtained, 16 g of α-hydroxy octanoic acid were slowly added, with stirring, to the glucosamine base solution. It was noted that the reaction was slightly exothermic since the temperature rose to 35° C. The reaction mixture was filtered and the water was removed by freeze-drying at a pressure of about 200 milliTorre and a temperature of about −45° C. 33 g of an off-white crystalline powder were obtained. The product was placed in a capped bottle that was placed in the refrigerator. The product kept in the refrigerator remained off-white in color after six months. A sample of the product was placed in an open dish exposed to the air at ambient temperature. The sample developed a yellow color after 3 days of such exposure.

EXAMPLE 2

Example 1 was repeated using 300 cc of purified water to which 16.5 g of polyethylene glycol homopolymer had been added. 49 g (97.2% yield) of the white salt product were obtained. A sample of this product was placed in an open dish exposed to the air at ambient temperature. The sample remained white in color after 7 days of such exposure.

EXAMPLE 3

150 cc of methylene chloride were placed in a beaker and 3.8 g (0.02 mole) of citric acid were added, with stirring at 20° C., thereby obtaining a solution. Thereafter, 3.6 g (0.02 mole) of halide-free glucosamine base were added, with stirring at 20° C. to the methylene chloride solution over a 5-minute period. The reaction mixture was stirred at 20° C. for an additional 60 minutes; it was noted that during this stirring step, the glucosamine base slowly went into solution. The methylene chloride was then stripped off under vacuum at 30° C. using a rotary evaporator. The resultant salt weighed 7 g and had a light yellow color. The product was placed in a capped bottle that was placed in a refrigerator and such product was used for comparison against a coated version of the same product.

EXAMPLE 4

Example 3 was repeated using 7.4 g of polyethylene glycol homopolymer 4000 in the methylene chloride prior to the addition of the citric acid. The polymer-coated salt weighed 14 g and had a white color. The Example 3 and 4 products were then compared for stability as set forth below.

A sample of the Example 3 product was placed in a dish exposed to the air at ambient temperature. The Example 3 product developed a yellow-orange color after 1 day of such exposure. A sample of the Example 4 product was placed in a dish exposed to the air at ambient temperature. The Example 4 product retained its white color after 7 days of such exposure.

What is claimed is:

1. A salt of a glucosamine base having a purity of at least 99 wt. % and a maximum halide content of 0.01 wt. %, and an organic acid selected from the group consisting of a hydroxyacid, a ketoacid and mixtures thereof.

2. A composition consisting essentially of the salt of claim 1 and a pharmaceutically acceptable polymer.

3. The composition of claim 2 wherein the polymer consists essentially of a water-soluble, water-dispersible and/or a water-swellable homopolymer and/or copolymer.

4. The composition of claim 2 wherein the polymer is selected from the group consisting of carboxypolymethylene homopolymers and copolymers; polyethylene glycol homopolymers and copolymers; polypropylene glycol homopolymers and copolymers; ethylcellulose; povidone homopolymers and copolymers; polyacrylic acid homopolymers and copolymers; polyacrylamide homopolymers and copolymers; polysaccharides; and mixtures of two or more of the foregoing polymers.

5. The composition of claim 2 wherein the polymer is present in an amount of about 2 to about 70 parts by weight, per part of the salt.

6. The salt of claim 1 wherein the hydroxyacid is selected from the group consisting of alkyl alpha hydroxyacids; aryl alpha hydroxyacids; aralkyl alpha hydroxyacids; polyhydroxy alpha hydroxyacids; polycarboxylic alpha hydroxyacids; beta hydroxyacids; and mixtures thereof.

7. A composition consisting essentially of a coated salt of a glucosamine base having a purity of at least about 99 wt. % and a maximum halide content of about 0.01 wt. %, and an organic acid selected from the group consisting of a hydroxyacid, a ketoacid and mixtures thereof, said coating comprising a pharmaceutically acceptable polymer such that the coated salt will be stable upon exposure to the atmosphere or ambient temperature.

8. The composition of claim 7 wherein the polymer consists essentially of a water-soluble, water-dispersible and/or a water-swellable homopolymer and/or copolymer.

9. The composition of claim 7 wherein the polymer is selected from the group consisting of carboxypolymethylene homopolymers and copolymers; polyethylene glycol homopolymers and copolymers; polypropylene glycol homopolymers and copolymers; ethylcellulose; povidone homopolymers and copolymers; polyacrylic acid homopolymers and copolymers; polyacrylamide homopolymers and copolymers; polysaccharides; and mixtures of two or more of the foregoing polymers.

10. The composition of claim 7 wherein the polymer is present in the composition in an amount of about 2 to about 70 parts by weight, per part of the salt.

11. The composition of claim 7 wherein the hydroxyacid is selected from the group consisting of alkyl alpha hydroxyacids; aryl alpha hydroxyacids; aralkyl alpha hydroxyacids; polyhydroxy alpha hydroxyacids; polycarboxylic alpha hydroxyacids; beta hydroxyacids; and mixtures thereof.

12. A method for preparing a salt of a glucosamine base having a purity of at least 99 wt. % and a maximum halide content of 0.01 wt. %, and an organic acid selected from the group consisting of a hydroxyacid, a ketoacid and mixtures thereof, comprising the steps of:
    (a) dissolving the glucosamine base in water;
    (b) adding a stoichiometric amount of an organic acid to the aqueous solution resulting from step (a); and
    (c) recovering the salt from the reaction mixture produced in step (b).

13. The method of claim 12 further comprising adding a pharmaceutically acceptable polymer to the solution resulting from step (a) prior to carrying out step (b) such that a stabilized salt is recovered in step (c).

14. The method of claim 13 wherein the pharmaceutically acceptable polymer comprises a water-soluble, water-dispersible and/or a water-swellable homopolymer and/or copolymer.

15. The method of claim 13 wherein the pharmaceutically acceptable polymer is selected from the group consisting of carboxypolymethylene homopolymers and copolymers; polyethylene glycol homopolymers and copolymers; polypropylene glycol homopolymers and copolymers; ethylcellulose; povidone homopolymers and copolymers; polyacrylic acid homopolymers and copolymers; polyacrylamide homopolymers and copolymers; polysaccharides; and mixtures of two or more of the foregoing polymers.

16. The method of claim 13 wherein the pharmaceutically acceptable polymer is added to the reaction mixture in an amount of about 2 to about 70 parts by weight, per part of the salt.

17. The method of claim 12 wherein step (c) is carried out by adding a water-miscible solvent to the reaction mixture so as to precipitate the salt therefrom.

18. The method of claim 12 wherein step (c) is carried out by freeze-drying.

19. The method of claim 12 wherein the hydroxyacid is selected from the group consisting of alkyl alpha hydroxyacids; aryl alpha hydroxyacids; aralkyl alpha hydroxyacids; polyhydroxy alpha hydroxyacids; polycarboxylic alpha hydroxyacids; beta hydroxyacids; and mixtures thereof.

\* \* \* \* \*